United States Patent [19]

Bourgogne et al.

[11] Patent Number: 5,705,193
[45] Date of Patent: Jan. 6, 1998

US005705193A

[54] METHOD FOR PREPARING GRANULES CONTAINING ONE OR MORE ACTIVE PRINCIPLES

[75] Inventors: Michel Bourgogne; Colette Meinard, both of Marseille, France

[73] Assignee: Roussel Uclaf, France

[21] Appl. No.: 666,549

[22] PCT Filed: Dec. 21, 1994

[86] PCT No.: PCT/FR94/01506

§ 371 Date: Jun. 20, 1996

§ 102(e) Date: Jun. 20, 1996

[87] PCT Pub. No.: WO95/17089

PCT Pub. Date: Jun. 29, 1995

[30] Foreign Application Priority Data

Dec. 22, 1993 [FR] France ................... 93 15413

[51] Int. Cl.$^6$ ........................................ A61K 9/14
[52] U.S. Cl. ................... 424/489; 424/405; 424/409; 424/408; 424/470
[58] Field of Search .......................... 424/409, 489, 424/408, 405, 406, 455, 470; 260/465; 71/96

[56] References Cited

U.S. PATENT DOCUMENTS

| 4,261,921 | 4/1981 | Smeltz .................... 260/465 |
| 4,913,722 | 4/1990 | Felix et al. ................ 71/90 |

FOREIGN PATENT DOCUMENTS

| 9008467 | 8/1993 | Australia . |
| 0127773 | 12/1984 | European Pat. Off. . |
| 0213328 | 3/1987 | European Pat. Off. . |
| 2210884 | 6/1989 | United Kingdom . |
| 9314631 | 8/1993 | WIPO . |

*Primary Examiner*—Thurman K. Page
*Assistant Examiner*—William E. Benston, Jr.
*Attorney, Agent, or Firm*—Bierman, Muserlian & Lucas

[57] ABSTRACT

A process for the preparation of granules containing at least one active principle with a melting point above 70° C. selected from the group consisting of herbicides, fungicides and insecticides comprising dissolving the active principle in an aromatic solvent or pyrrolidone, absorbing the resulting solution on a support, optionally adding water thereto and drying the resulting product to form the granules and the granules produced thereby which have a superior biological activity than a granule dispersible in water with good stability.

11 Claims, No Drawings

METHOD FOR PREPARING GRANULES CONTAINING ONE OR MORE ACTIVE PRINCIPLES

The present invention relates to a new process for preparing emulsions or suspo-emulsions, dry or extruded in the form of granules, and the granules thus obtained.

The presentation of the active material in the form of an emulsion allows granules to be obtained which are endowed with a biological activity superior to that of a granule dispersible in water obtained by drying of a concentrated suspension of an active principle.

The subject of the invention is a process for preparing granules containing one or more active principles characterized in that the said active principle or principles is or are dissolved in a solvent, a solution is obtained which is absorbed on a support (or a filler) which may contain another active principle, a product is obtained to which water is or is not added, and which is dried and given the form of granules.

The support or filler can be chosen from the group of the following products: clays, bentonites, lactoses, starches, silicas, silicates, sulphates, and chlorides of alkaline and alkaline-earth metals.

In a preferred embodiment, the quantity of support used is less than 60% (m/m) of the total quantity of the ingredients used.

Citable as solvent are aromatic hydrocarbons, such as 1-methylnaphthalene, tetrahydronaphthalene, decahydronaphthalene, 2-methylnaphthalene or dimethylnaphthalene, alkylbenzenes, xylene (including Solvesso 200®), mixtures of isomers of dibenzyltoluene such as Marlotherm S®) or mixtures of isomers of benzyltoluene such as Marlotherm L®, aliphatic hydrocarbons, mineral or vegetable oils, alcohols such as cyclohexanol, C8 alcohols, ethers such as dibenzylether, ketones such as cyclohexanone or 4-methylcyclohexanone, amides such as N,N-dimethylcaprylamide capramide (HALLCOMID® M 8-10), esters such as alkyl benzoates (ethyl, propyl, n-butyl for example), mono and dialkyl phthalates (of ethyl, of propyl or of n-butyl, for example), pyrrolidones such as N-methylpyrrolidone, N-octylpyrrolidone (AG SOL EX 8®), N-dodecylpyrrolidone (AG SOL EX 12®), N-cyclohexylpyrrolidone or mixtures of these solvents, such as Surfadone LP 100®. Also citable are TBP or tributyl phosphate, dibenzylether, N-butyl benzoate.

Citable as preferred solvent are aromatic solvents such as Solvesso 200®, or pyrrolidones such as Surfadone LP 100®.

In a preferred embodiment, the quantity of solvent used is between 20 and 40% (m/m) of the total quantity of the ingredients used.

The active principle can be of a very varied nature: it is preferably a pesticide.

The subject of the invention is in particular the process characterized in that the active principle is a herbicide, an insecticide or a fungicide.

The subject of the invention is more particularly the process characterized in that the active principle has a melting point above 70° C.

The subject of the invention is quite particularly a process which is characterized in that the active principle is a pyrethrinoid. The latter can be alone or associated with other active principles such as pyrimicarb or the derivatives of β-methoxy acrylic acid or the lipidamides.

Among the pyrethrinoids usable for the preparation of the granules of the invention can be cited deltamethrin, cypermethrin, alphamethrin, tralomethrin, cyalothrine, fenvalerate, cyfluthrine, flucythrinate, fluvalinate, fenpropathrine, tefluthrine, bifenthrine, acrinathrine, esfenvalerate, betacyfluthrine, taufluvalinate or lambdacyhalothrine.

Deltamethrin can be cited as preferred pyrethrinoid.

In a preferred embodiment, the quantity of active principle used is less than 20% of the total quantity of the ingredients used.

The subject of the invention is in particular a preparation process which is characterized in that one or more of the following ingredients is added to the solvent: emulsifiers and stabilizers.

The subject of the invention is also a process which is characterized in that one or more of the following elements is also added: dispersants, wetting agents, binders, colorants, anti-foaming agents and adjuvants facilitating extrusion or lubricants.

Citable as emulsifiers are anionic emulsifiers such as calcium dodecylbenzene sulphonate or the phosphoric esters or non-ionic emulsifiers such as copolymers of ethylene oxide and propylene oxide, ethoxylated castor oil or ethoxylated fatty alcohols.

Citable as stabilizers are anti-oxidants such as butylhydroxytoluene or acids such as citric acid or acetic acid.

The dispersing agent can be an ionic or non-ionic surfactant or a mixture of such surfactants.

Citable as compounds that can be used as dispersing agent are for example polymers of the arylsulphonate type, in particular the alkaline polynaphthalene sulphonates obtained by condensation of (alkyl) aryl sulphonate derivatives with formaldehyde, lignosulphonates (for example: sodium lignosulfonate and calcium lignosulphate), the polyphenol sulphonates, the salts of polyacrylic acids, the salts of lignosulphonic acids (for example: the sodium salt of polymerized lignosulphonic acids of the Kraft type), the salts of sulphonic phenol acids or sulphonic naphthalenes, the phosphoric esters of alcohols or of polyethoxylated phenols, the esters of fatty acids and of polyols, derivatives with a sulphates, sulphonates and phosphates function of the preceding compounds.

The wetting agent can be an ionic or non-ionic surfactant or a mixture of such surfactants.

Citable as compounds that can be used as wetting agent are, for example, the salts of the alkyl sulphate type (for example: sodium lauryl sulphate (SIPON LCS 98®), the salts of the alkyl ether sulphate type (for example: sodium lauryl ether sulphate), the salts of the alkyl aryl sulphonate type, in particular the alkaline alkylnaphthalene sulphonates, the salts of polycarboxylic acids, the polycondensates of ethylene oxide on fatty alcohols or on fatty acids or on fatty amines, the substituted phenols, in particular the alkylphenols or arylphenols, the salts of esters of sulphosuccinic acids, the salts of α-olefins sulphonates, derivatives of taurine, in particular alkyltaurates (for example: oleyl methyltaurate).

Citable as an agent promoting extrusion or lubricant is magnesium stearate or talc.

Citable as binder are sugars, polyvinyl and polyalkyl pyrrolidones, carboxymethyl cellulose and xanthan gum.

Silicones can be used as anti-foaming agents.

The subject of the invention is quite particularly a process, characterized in that there are used:
less than 50% of active principle m/m
20 to 40% of solvent m/m
0 to 5% of emulsifier m/m
0 to 5% of stabilizer m/m
0 to 15% of dispersant m/m 0 to 10% of wetting agent m/m
0 to 5% of binder m/m
0 to 1% of lubricant m/m.

The granules thus obtained are in themselves a subject of the present invention.

The granules obtained according to the invention are easy to prepare, easy to use and present a good stability as well as a good biological activity.

The granules obtained according to the invention can be used in the field:
- of agriculture for the treatment of crops,
- of animals,
- of the environment.

Pesticide compositions intended for the treatment of crops can be obtained very easily, by dispersing the granules in water.

It is possible for example to spread 50 to 1000 g per hectare of compositions prepared in this way, i.e. a dose per hectare of between 5 and 100 g of pyrethrinoid for example.

The granules of the invention preferably have a granulometry between 1 and 10 mm, for example between 2 and 6 mm.

The following examples illustrate the invention.

A—Preparation of the Granules of the Invention

The active material is dissolved in a solvent possibly comprising other elements (emulsifier, stabilizer).

The solution obtained is absorbed on a support (also called filler) possibly containing other elements (dispersant, wetting agent, binder). This is moistened by adding water in order to obtain a paste which is forced through a die. Extrudates are thus obtained, which are dried and cut to the desired size.

Procedure:
1—Dissolution accompanied by magnetic stirring of the active material in the solvent with possibly emulsifiers and stabilizers.
2—Mixing of the solid ingredients (fillers), dispersants, wetting agents, binders and possibly other active materials, in a homogenizer for powders.
3—Spraying of the organic solution of active material onto the solid filler (this can also be carried out on silica and then mixing with other ingredients).
4—Possibly grinding or deglommeration of the obtained product.
5—Moistening of the obtained powder with 0 to 50 g of water per 100 g of powder, preferably 10 to 20 g.
6—Extrusion on a die with holes of 0.5 to 3 mm (preferably 1 mm).
7—Drying of the obtained extracts on a fluidized-air bed at temperatures between 20° and 150° C. (preferably 50° to 60° C.). Drying can take place in a stove, at ambient temperature, or in a microwave oven.
8.—Cutting to the desired dimension.

Granules were prepared according to the procedure described above using the following ingredients:

EXAMPLE 1

| INGREDIENTS | % m/m |
|---|---|
| Deltamethrin ® | 3.27 |
| Calcium phenylsulphonate ® | 1.07 |
| Emulsogen EL 360 ® | 1.61 |
| Solvesso 200 ® | 32.40 |
| Wessalon S ® | 20.65 |
| Sipon LCS 98 ® | 3.00 |
| Geropon T 36 ® | 7.00 |
| Argirec B 24 ® | 31.00 |

EXAMPLE 2

| INGREDIENTS | % m/m |
|---|---|
| Deltamethrin ® | 5.13 |
| Soprofor PA 17 ® | 3.48 |
| Genapol PF 10 ® | 0.38 |
| Surfadone LP 100 ® | 28.61 |
| Wessalon S ® | 20.00 |
| Sipon LCS 98 ® | 3.00 |
| Geropon T 36 ® | 5.00 |
| BHT | 0.04 |
| Citric acid | 0.004 |
| Weegum F ® | 3.00 |
| Maize starch | 31.36 |

EXAMPLE 3

| INGREDIENTS | % m/m |
|---|---|
| Deltamethrin ® | 5.13 |
| Soprofor PA 17 ® | 3.48 |
| Genapol PF 10 ® | 0.38 |
| Surfadone LP 100 ® | 28.61 |
| Wessalon S ® | 20.00 |
| Sipon LCS 98 ® | 3.00 |
| Geropon T 36 ® | 5.00 |
| BHT | 0.04 |
| Citric acid | 0.004 |
| Sodium sulphate | 3.00 |
| Maize starch | 29.36 |
| Borresperce NA ® | 2.00 |

EXAMPLE 4

| INGREDIENTS | % m/m |
|---|---|
| Deltamethrine ® | 5.13 |
| Soprofor PA 17 ® | 3.48 |
| Genapol PF 10 ® | 0.38 |
| Surfadone LP 100 ® | 28.61 |
| Wessalon S ® | 25.64 |
| Sipon LCS 98 ® | 5.00 |
| Geropon T 36 ® | 10.00 |
| BHT | 0.04 |
| Citric acid | 0.004 |
| Sodium sulphate | 10.90 |
| Sugar | 10.00 |

EXAMPLE 5

| INGREDIENTS | % m/m |
|---|---|
| Deltamethrin ® | 5.13 |
| Soprofor PA 17 ® | 3.48 |
| Genapol PF 10 ® | 0.38 |
| Surfadone LP 100 ® | 28.61 |
| Wessalon S ® | 25.64 |
| Sellogen DFL ® | 5.00 |

-continued

| INGREDIENTS | % m/m |
|---|---|
| Reax 88 A ® | 3.00 |
| BHT | 0.04 |
| Citric acid | 0.004 |
| Light maize dextrin | 10.00 |
| Argirec B 24 ® | 17.90 |

EXAMPLE 6

| INGREDIENTS | % m/m |
|---|---|
| Deltamethrin ® | 5.13 |
| Soprofor PA 17 ® | 3.48 |
| Genapol PF 10 ® | 0.38 |
| Surfadone LP 100 ® | 28.61 |
| Wessalon S ® | 25.64 |
| Morwet D 425 ® | 5.00 |
| Sipon LCS 98 ® | 3.00 |
| BHT | 0.04 |
| Citric acid | 0.004 |
| Bentone EW ® | 5.00 |
| Argirec B 24 ® | 22.90 |

EXAMPLE 7

| INGREDIENTS | % m/m |
|---|---|
| Deltamethrin ® | 3.1 |
| Pirimicarb ® | 47.1 |
| BHT | 0.02 |
| Citric acid | 0.002 |
| Rhodafac PA 17 ® | 2.09 |
| Agsolex 8 ® | 17.89 |
| Wessalon S ® | 15.00 |
| SI dispersant | 10.00 |
| Maize starch | 4.8 |

Calcium phenylsulphonate=calcium dodecylbenzenesulphonate:emulsifier

Emulsogen EL 360®=ethoxylated castor oil:emulsifier
Solvesso 200®=alkylnapthalenes:solvent
Wessalon S®=silica:filler
Sipon LCS 98®=Na lauryl sulphate:wetting agent
Geropon T 36®=polycarboxylate:dispersant—binder
Argirec B 24®=kaolin clay:filler
Soprofor PA 17® (Rhodafac PA 17®)=ethoxylated alkylaryl phosphate ether:emulsifier
Genapol PF 10®=EO/PO block copolymer:emulsifier
Surfadone LP 100®=N-alkylpyrrolidone:solvent
BHT=butylhydroxytoluene:stabilizer
Weegum F®=silicate of Al and Mg:filler-binder
Borresperce Na®=lignosulphate of Na:dispersant
Sellogen DFL®=sulphonate alkylnaphthalene of Na:wetting agent
Reax 88 A®=lignosulphonate of Na:dispersant
Morwet D 425®=alkylnaphthalene sulphonate of Na:dispersant
Bentone EW®=silicate of Mg:filler-binder
Agsolex 8®=N-alkyl pyrrolidone
SI dispersant=mixture of sodium N-alkyl naphthalene and sodium lauryl sulphate.

B—Stability study

The behaviour in storage of the granules of the invention was studied.

These granules are kept for 4 weeks at 50° C. and for 6 weeks observing a cycle according to which the temperature is kept at −6° C. for 6 hours, increased to +46° C. in 6 hours, and kept at −6° C. for 6 hours and so on for 6 weeks. These granules keep their initial properties. The following characteristics did not in fact change significantly: appearance, dispersability, deltamethrin content, dilution.

The granules have a very good stability.

Biological Study of the Granules of the Invention

1—The granules described above are mixed with water at the rate of 0.5 to 0.75 kg of granules for volumes varying from 150 to 500 liters of water, preferably varying between 250 and 300 liters of water. Diluted pulps are thus obtained, which are sprayed at the rate of 250–300 l/ha onto different infested crops (cereals, colza, peas, beet, vegetable crops). An excellent insecticidal activity is obtained on these different crops.

2—Activity on aphids

The methodology used is the following.

Wingless females of the first and second larval stage of Rhopalosiphum padi are used, and stage 2F wheat seedlings (Florence-Aurore variety), grown in pots (8 plants per pot).

2 days before treatment, each pot is infested with 16 adult aphids.

1 day and 6 days after treatment (1D AT, 6D AT) the aphids are counted.

The results obtained are the following:

| | 1 D AT | | 6 D AT | |
|---|---|---|---|---|
| | Adult aphids/pot | % effectiveness | Aphids /pot | % effectiveness |
| CONTROL Concentration 4.1% | 13.5 ± 0.9 | — | 72.6 ± 21.5 | — |
| 6.25 g a.m./ha | 1.25 ± 1.2 | 91 | 13.7 ± 4.9 | 81 |
| 3.125 g a.m./ha | 2.6 ± 0.8 | 80 | 16.5 ± 6.5 | 77 | a.m. = active material

We claim:

1. A process for the preparation of granules containing at least one active principle with a melting point above 70° C. selected from the group consisting of herbicides, fungicides and insecticides comprising dissolving the active principle in an aromatic solvent or pyrrolidone, absorbing the resulting solution on a support, optionally adding water thereto and drying the resulting product to form the granules.

2. The process of claim 1 wherein the support is selected from the group consisting of clays, bentonites, lactose, starch, silica and alkali metal and alkaline earth metal silicates, sulfates and chlorides.

3. The process of claim 1 wherein the support is less than 60% (m/m) of the granules.

4. The process of claim 1 wherein the solvent is 20 to 40% (m/m) of the granules.

5. The process of claim 1 wherein the active principle is a pyrethrinoid.

6. The process of claim 1 wherein the active ingredient is deltamethrin.

7. The process of claim 1 wherein the active principle is 20% by weight of the granules.

8. The process of claim 1 wherein the aromatic solvent or pyrrolidone contains at least one member of the group consisting of emulsifiers and stabilizers.

9. The process of claim 1 wherein the aromatic solvent or pyrrolidone contains at least one member of the group consisting of dispersants, wetting agents, binders, colorants, antifoaming agents, lubricants and extrusion adjuvants.

10. Granules obtained by the process of claim 1.

11. Granules of claim 10 containing less than 50% (m/m) of active principle, 20 to 40% (m/m) of aromatic solvent or pyrrolidone, 0 to 5% (m/m) of emulsifier, 0 to 5% (m/m) of stabilizer, 0 to 15% (m/m) of dispersant, 0 to 10% (m/m) of wetting agent, 0 to 5% (m/m) of binder and 0 to 1% (m/m) of lubricant.

* * * * *